(12) United States Patent
Freudenberger et al.

(10) Patent No.: US 10,470,740 B2
(45) Date of Patent: Nov. 12, 2019

(54) MOVING A ROBOT ARM

(71) Applicant: Siemens Healthcare GmbH, Erlangen (DE)

(72) Inventors: Joerg Freudenberger, Kalchreuth (DE); Sultan Haider, Erlangen (DE); Peter Molnar, Nuenberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 15/986,907

(22) Filed: May 23, 2018

(65) Prior Publication Data
US 2018/0344284 A1 Dec. 6, 2018

(30) Foreign Application Priority Data

May 31, 2017 (EP) ..................................... 17173787

(51) Int. Cl.
*A61B 34/20* (2016.01)
*A61B 8/00* (2006.01)
(Continued)

(52) U.S. Cl.
CPC .......... *A61B 8/4218* (2013.01); *A61B 8/4263* (2013.01); *A61B 8/467* (2013.01);
(Continued)

(58) Field of Classification Search
USPC ................................................ 700/245–264
See application file for complete search history.

(56) References Cited

U.S. PATENT DOCUMENTS

| 5,919,135 A * | 7/1999 | Lemelson | A61B 5/055 |
| | | | 378/4 |
| 9,420,997 B2 * | 8/2016 | Wong | G01S 15/8981 |

(Continued)

FOREIGN PATENT DOCUMENTS

| CN | 101530338 A | 9/2009 |
| CN | 104856720 A | 8/2015 |

(Continued)

OTHER PUBLICATIONS

"Ultrasound robots go the distance"; in; http://invenio.deakin.edu.au/ultrasound-robots-go-the-distance/;pp. 1-5; 2017.
(Continued)

*Primary Examiner* — Jonathan L Sample
(74) *Attorney, Agent, or Firm* — Harness, Dickey & Pierce, P.L.C.

(57) ABSTRACT

A method is disclosed for moving a robot arm for an ultrasound examination, an ultrasound probe being attached to the robot arm. An associated ultrasound system is also disclosed. In an embodiment, the method includes providing a trained artificial neural network recording a medical issue; determining a motion dataset containing a motion sequence of the robot arm by applying the trained artificial neural network to the medical issue; transferring the motion dataset to a controller of the robot arm; and moving the robot arm in accordance with the motion sequence of the motion dataset. An associated second computing unit, and an associated computer program product are also disclosed.

13 Claims, 2 Drawing Sheets

(51) Int. Cl.
   *G06N 3/02* (2006.01)
   *A61B 34/30* (2016.01)
   *A61B 34/32* (2016.01)
   *G16H 30/20* (2018.01)
   *B25J 9/16* (2006.01)
   *B25J 11/00* (2006.01)
   *A61B 90/00* (2016.01)
   *A61B 34/10* (2016.01)

(52) U.S. Cl.
   CPC .............. *A61B 8/54* (2013.01); *A61B 34/30* (2016.02); *A61B 34/32* (2016.02); *B25J 9/1664* (2013.01); *B25J 11/008* (2013.01); *G06N 3/02* (2013.01); *G16H 30/20* (2018.01); *A61B 8/429* (2013.01); *A61B 8/463* (2013.01); *A61B 2034/107* (2016.02); *A61B 2034/2048* (2016.02); *A61B 2034/2059* (2016.02); *A61B 2090/061* (2016.02); *A61B 2090/065* (2016.02); *Y10S 901/09* (2013.01); *Y10S 901/30* (2013.01)

(56) References Cited

U.S. PATENT DOCUMENTS

| | | | | |
|---|---|---|---|---|
| 9,840,003 | B2* | 12/2017 | Szatmary | B25J 5/00 |
| 9,849,593 | B2* | 12/2017 | Wang | B25J 9/1689 |
| 9,956,690 | B2* | 5/2018 | Wang | G05D 1/0038 |
| 2004/0243147 | A1* | 12/2004 | Lipow | G09B 23/28 |
| | | | | 606/130 |
| 2005/0154295 | A1* | 7/2005 | Quistgaard | A61B 5/6843 |
| | | | | 600/424 |
| 2007/0021738 | A1* | 1/2007 | Hasser | A61B 90/37 |
| | | | | 606/1 |
| 2008/0010706 | A1 | 1/2008 | Moses | |
| 2009/0088639 | A1* | 4/2009 | Maschke | A61B 8/4218 |
| | | | | 600/443 |
| 2009/0234444 | A1 | 9/2009 | Simens | |
| 2013/0172906 | A1* | 7/2013 | Olson | A61B 34/71 |
| | | | | 606/130 |
| 2013/0218340 | A1* | 8/2013 | Hager | B25J 9/1671 |
| | | | | 700/257 |
| 2013/0329038 | A1* | 12/2013 | Hager | B25J 9/1697 |
| | | | | 348/113 |
| 2014/0046128 | A1 | 2/2014 | Lee | |
| 2014/0081659 | A1* | 3/2014 | Nawana | G06F 19/00 |
| | | | | 705/3 |
| 2016/0375592 | A1* | 12/2016 | Szatmary | B25J 5/00 |
| | | | | 700/255 |
| 2017/0011185 | A1* | 1/2017 | Schweizer | G06F 19/321 |
| 2017/0258526 | A1* | 9/2017 | Lang | H05K 999/99 |

FOREIGN PATENT DOCUMENTS

| | | |
|---|---|---|
| DE | 102015212953 A1 | 1/2017 |
| EP | 2514366 A1 | 10/2012 |
| WO | WO 2017020081 A1 | 2/2017 |

OTHER PUBLICATIONS

"MELODY, a remote, robotic ultrasound solution"; in: http://www.adechotech.com/products; pp. 1-13; 2017.

Extended European Search Report #17173787.7 dated Nov. 13, 2017.

Extended European Search Report and English translation thereof dated Nov. 13, 2017.

European Intention to Grant and English translation thereof dated Jan. 7, 2019.

Chinese Office Action and English translation thereof dated Jul. 23, 2019.

* cited by examiner

MOVING A ROBOT ARM

PRIORITY STATEMENT

The present application hereby claims priority under 35 U.S.C. § 119 to European patent application number EP 17173787.7 filed May 31, 2017, the entire contents of which are hereby incorporated herein by reference.

FIELD

At least one embodiment of the invention generally relates to a method for moving a robot arm for an ultrasound examination, an ultrasound probe being attached to the robot arm. At least one embodiment of the invention further generally relates to an associated ultrasound system, a method for providing a trained artificial neural network, an associated second computing unit, and an associated computer program product.

BACKGROUND

Typically, an ultrasound system enables a body that is to be examined of an examination subject, in particular a human patient, to be examined non-invasively. An ultrasound system for medical diagnostics typically comprises an ultrasound probe which is placed onto a body surface of the patient by a physician and, in close contact with the skin of the patient, generates an ultrasound image. For this purpose, the ultrasound probe contains a one-dimensional or two-dimensional piezoelectric array in which electrical transmit pulses are converted into pressure pulses at a specific frequency or in a specific frequency band or, as the case may be, pressure pulses are converted into electrical receive signals. Normally, ultrasound images can be generated from the electrical receive signals, the ultrasound images usually being visualized in a specific mode.

Typically, the ultrasound probe is moved during an ultrasound examination. A method is described in U.S. Pat. No. 9,420,997 B2 in which motion artifacts may be suppressed in ultrasound diagnostic imaging.

A combination of a robot arm with an ultrasound probe is disclosed in WO 2017 020 081 A1.

Artificial neural networks have been a focus of attention in science and industry for some considerable time already. Artificial neural networks are modeled on the natural neural networks which are formed by nerve cell interconnections in the brain and spinal cord. An artificial neural network typically comprises a plurality of nodes and connections between nodes. In a training phase, the neural network is able to learn based on changes that are made to weightings of the connections. Typically, artificial neural networks deliver better results in challenging applications than competing machine learning methods.

DE 10 2015 212 953 A1 describes a possible application of a trained artificial neural network.

SUMMARY

Embodiments of the invention disclose a method for moving a robot arm for an ultrasound examination, an ultrasound probe being attached to the robot arm, an associated ultrasound system, a method for providing a trained artificial neural network, an associated second computing unit, and an associated computer program product.

Advantageous developments are disclosed in the claims.

Embodiments of the invention relate to the ultrasound system and the method for moving the robot arm for an ultrasound examination and in relation to the method for providing the trained artificial neural network, as well as to the second computing unit and the associated computer program product. Features, advantages or alternative embodiment variants mentioned in this regard are also to be applied to the other claimed subject matters, and vice versa. In other words, the object-related claims (which are directed for example to an ultrasound system) may also be developed using the features described or claimed in connection with a method. The corresponding functional features of the method are in this case embodied by corresponding object-related modules.

The method according to at least one embodiment of the invention for moving a robot arm for an ultrasound examination, an ultrasound probe being attached to the robot arm, comprises:
provide a trained artificial neural network,
recording a medical issue,
determining a motion dataset containing a motion sequence of the robot arm by applying the trained artificial neural network to the medical issue,
transferring the motion dataset to a controller of the robot arm, and
moving the robot arm in accordance with the motion sequence of the motion dataset.

At least one embodiment of the method for providing a trained artificial neural network for the purpose of determining a motion dataset containing a motion sequence of a robot arm for an ultrasound examination, an ultrasound probe being attached to the robot arm, comprises:
providing at least one training motion dataset, wherein at least one medical training issue is assigned to the at least one training motion dataset,
training an artificial neural network using the at least one training motion dataset and the at least one medical training issue,
wherein the application of the trained artificial neural network to the at least one medical training issue enables the at least one training motion dataset to be determined, and
providing the trained artificial neural network for the purpose of determining the motion dataset.

The ultrasound system of at least one embodiment comprises a planning unit, a first computing unit and a measurement unit which has a robot arm for an ultrasound examination, an ultrasound probe being attached to the robot arm.

The planning unit may comprise the monitor with the graphical user interface and the input device. Typically, the user is able to interact with the planning unit, in particular via the input device. For example, the user may also view ultrasound measurement data or ultrasound images of the ultrasound examination on the monitor. The planning unit can display ultrasound measurement data in particular on the monitor.

The first computing unit is preferably configured in such a way that it can determine the motion dataset by applying the artificial neural network to the medical issue. The computing unit may have interfaces to the planning unit, to the controller or to the measurement unit, wherein the medical issue and/or the motion dataset can in particular be received and sent via the interfaces. The first computing unit is preferably embodied in such a way that the trained neural network, which is provided for example as a computer program product and can be loaded into a memory of the first programmable computing unit, is executable on the first computing unit.

The measurement unit comprises the robot arm for the ultrasound examination. The ultrasound probe is attached to the robot arm. The measurement unit normally comprises the robot arm and the controller of the robot arm. The measurement unit may comprise the sensor, the camera and/or the projector. The ultrasound system is preferably embodied for moving the robot arm for the purpose of the ultrasound examination.

Most of the components of the ultrasound system according to at least one embodiment of the invention may be embodied in the form of software components. In principle, however, some of these components may also be realized in the form of software-assisted hardware components, for example FPGAs or the like, in particular when there is a requirement for particularly fast calculations. Similarly, the required interfaces may be embodied as software interfaces, for example when it is simply a matter of importing data from other software components. However, they may also be embodied as hardware-based interfaces which are controlled by suitable software. It goes without saying that it is also conceivable for a plurality of the cited components to be realized in combination in the form of a single software component or software-assisted hardware component.

The second computing unit according to at least one embodiment of the invention is embodied for providing a trained artificial neural network for the purpose of determining a motion dataset containing a motion sequence of a robot arm for an ultrasound examination, an ultrasound probe being attached to the robot arm. Preferably, the second computing unit is able to perform a method according to the invention for providing a trained artificial neural network. The second computing unit comprises a computing module. The computing module may be used for example for the training of the artificial neural network.

The computer program product according to at least one embodiment of the invention can be loaded directly into a memory of a programmable computing unit and has program code segments for performing a method according to at least one embodiment of the invention when the computer program product is executed in the computing unit. The first computing unit and the second computing unit are equivalent to such a programmable computing unit and each have a memory.

The computer program product may be a computer program or comprise a computer program. This enables at least one embodiment of the method according to the invention to be performed quickly and in an identically reproducible and robust manner. The computer program product is configured in such a way that it can perform at least one embodiment of the inventive method steps by way of the computing unit. The computing unit must in each case provide the prerequisites for this, such as a corresponding random access memory, for example, a corresponding graphics card or a corresponding logic unit, so that the respective method steps can be performed efficiently.

The computer program product is stored, for example in at least one embodiment, on a non-transitory computer-readable medium or held resident on a network or server, from where it can be loaded into the processor of the computing unit, which processor may be embodied for example as part of the ultrasound system. Control information of the computer program product may also be stored on an electronically readable data medium. The control information of the electronically readable data medium may be embodied in such a way that it performs a method according to at least one embodiment of the invention when the data medium is used in a computing unit. Thus, the computer program product may also represent the electronically readable data medium.

BRIEF DESCRIPTION OF THE DRAWINGS

The invention is described and explained in more detail below with reference to the example embodiments depicted in the figures, in which.

DETAILED DESCRIPTION OF THE EXAMPLE EMBODIMENTS

Figure 1:
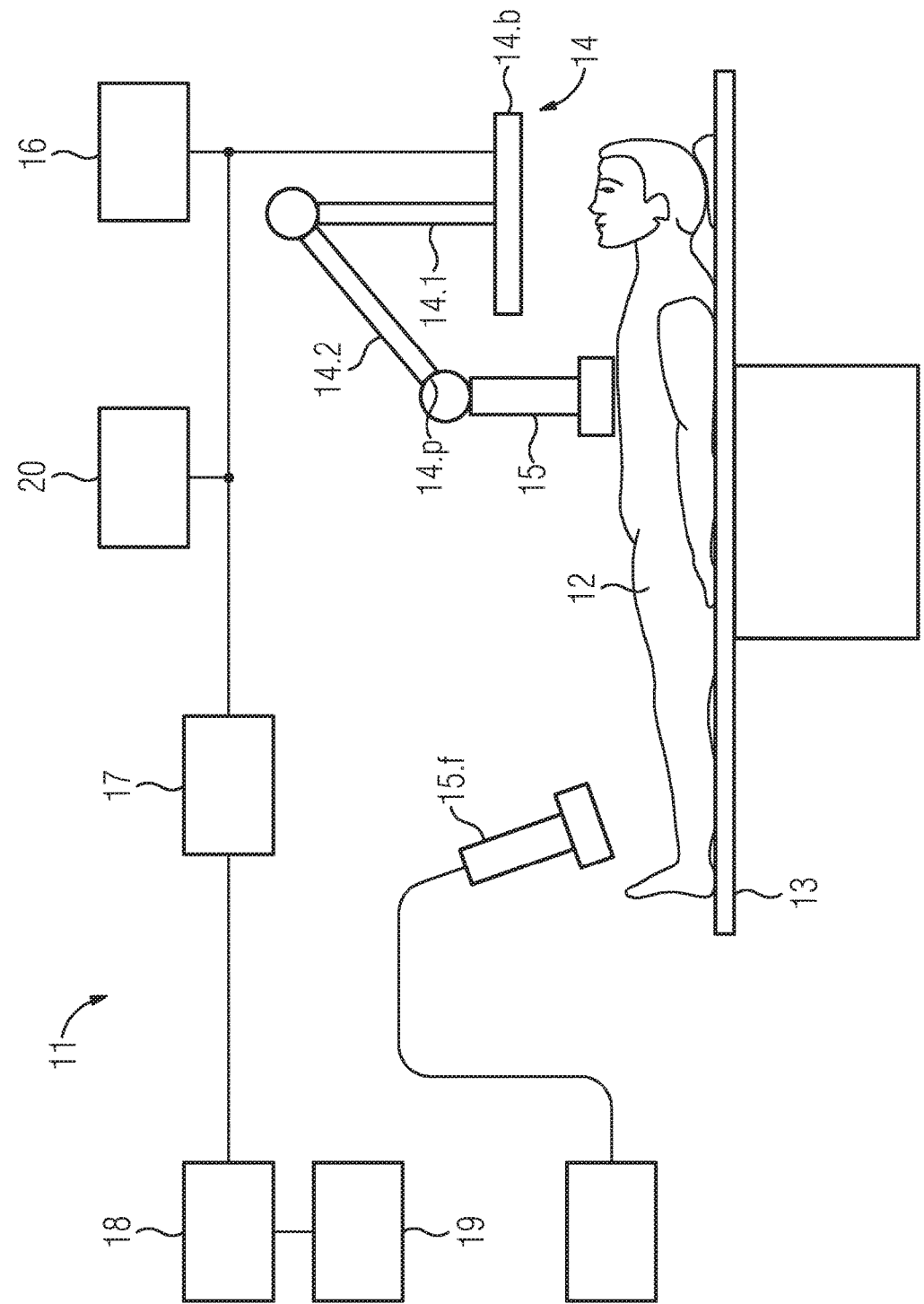
FIG. 1 shows an embodiment of an ultrasound system 11.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s)

as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The method according to at least one embodiment of the invention for moving a robot arm for an ultrasound examination, an ultrasound probe being attached to the robot arm, comprises:
  providing a trained artificial neural network,
  recording a medical issue,
    determining a motion dataset containing a motion sequence of the robot arm by applying the trained artificial neural network to the medical issue,
    transferring the motion dataset to a controller of the robot arm, and
  moving the robot arm in accordance with the motion sequence of the motion dataset.

The method according to at least one embodiment of the invention may in this way permit a better and more straightforward ultrasound examination. Embodiments of the invention may therefore offer in particular a number of advantages as follows.

For example, the robot arm can support a user during the movement and/or the robot arm is moved automatically. This is advantageous in particular when for example a user, in particular a physician, requires assistance during the ultrasound examination because the physician lacks experience or is not familiar with the ultrasound examination, or because the physician is simultaneously performing a surgical intervention. It is furthermore possible that in situations where no physician, and consequently no user familiar with the ultrasound examination, is available to perform the same, the ultrasound examination is performed automatically or even autonomously in that the robot arm is moved automatically.

Preferably, there is no need for the robot arm to be controlled remotely by an experienced specialist ultrasound physician. Furthermore, the high degree of repeatability in both methods for moving the robot arm should be emphasized, as a result of which a cost saving in the ultrasound examination and/or an actual execution of the ultrasound examination are at all possible in the first place. Owing to the high degree of repeatability, the robot arm is particularly advantageous for the ultrasound examination, the ultrasound probe being attached to the robot arm. For example, a screening of the cardiac function in a large population could be carried out thereby cost-effectively and with a high degree of automation.

An artificial neural network (ANN) is in particular a network composed of artificial neurons that is simulated in a computer program. Typically, the artificial neural network is in this case based on a networking of a plurality of artificial neurons. In this case the artificial neurons are typically arranged on different layers. The artificial neural network usually comprises an input layer and an output layer, the neuron output of which is rendered visible as the only output of the artificial neural network. Intermediate layers between the input layer and the output layer are typically referred to as hidden layers.

Typically, an architecture and/or topology of an artificial neural network are/is initiated in a first phase and then trained in a training phase for a specific task or in a training phase for a plurality of tasks. Typically, the training of the artificial neural network in this case comprises making a change to a weighting of a connection between two artificial neurons of the artificial neural network. The training of the artificial neural network may also comprise a development of new connections between artificial neurons, a deletion of existing connections between artificial neurons, an adjustment of threshold values of the artificial neurons, and/or an addition or a deletion of artificial neurons. Thus, two different trained artificial neural networks are able to perform different tasks even though, for example, they share the same architecture and/or topology.

One example of an artificial neural network is a shallow artificial neural network, which normally contains only a single hidden layer between the input layer and the output layer and is therefore relatively easy to train. Another example is a deep artificial neural network containing a plurality (for example up to ten) of interleaved hidden layers of artificial neurons between the input layer and the output layer. The deep artificial neural network in this case enables an improved recognition of patterns and complex interrelationships. Furthermore, a deep convolutional artificial neural network which additionally uses convolution filters, for example edge filters, may be chosen for determining a motion dataset.

It is now proposed, in at least one embodiment, that a trained artificial neural network embodied in this way be chosen, the application of the trained artificial neural network to the medical issue enabling a motion dataset to be determined. The trained artificial neural network may in this case be suitable only for determining the motion dataset by applying the trained artificial neural network to the medical issue. Alternatively, it may also take on other tasks. It may happen that different artificial neural networks are set up which are equally capable of performing the determination of the motion dataset.

In at least one embodiment of the present method, in particular an already trained artificial neural network is provided for determining the motion dataset by applying the trained artificial neural network to the medical issue. The training of the artificial neural network may in this case have been accomplished by way of at least one training motion dataset and by way of at least one medical training issue. Various options for training the artificial neural network are described in one of the following sections. Advantageously, the artificial neural network may be trained by way of a method according to the invention described in one of the following sections for providing a trained artificial neural network for the purpose of determining a motion dataset containing a motion sequence of a robot arm for an ultrasound examination, an ultrasound probe being attached to the robot arm.

The recording of the medical issue may entail a sensor, in particular a camera, providing at least one parameter of the medical issue. Alternatively or in addition, it is also conceivable that the recording of the medical issue comprises a user providing at least one parameter of the medical issue via a graphical user interface. Basically, it is also conceivable that both a sensor and a user provide at least one parameter of the medical issue.

The sensor, in particular an optical camera, may preferably be suitable for capturing images of a person to be examined, in particular a patient. An image recognition process may be performed by way of suitable and known algorithms. Preferably, the sensor may capture a plurality of images of the person to be examined, for example in a film recording. The image recognition process may also be applied to the film recording. At least one parameter of the medical issue may be acquired via the image recognition process, which parameters are provided for example by a controller of the sensor. The medical issue may include at least one parameter acquired via the image recognition process. Basically, it is also conceivable that the sensor has a plurality of sensor components, each of which features a different sensor technology.

The user may for example provide at least one parameter of the medical issue on a graphical user interface. For this purpose, a planning unit, for example, has a monitor, the monitor having the graphical user interface. Typically, the user may interact with the graphical user interface via an input device. Preferably, the graphical user interface may provide default values or a list containing typical values or parameters which the user may consult and select. Basically, it is also conceivable that the user may freely input or select at least one parameter of the medical issue. The at least one parameter of the medical issue may be provided completely by the sensor, completely by the user or partly by the sensor and partly by the user.

In a further embodiment, the medical issue includes at least one parameter from the following list:
a body region to be examined of a patient,
a mode of the ultrasound examination,
a frequency of the ultrasound examination, and
a specification for the ultrasound examination.

The body region to be examined of the patient may comprise a region or a part of the patient that is to be examined in the ultrasound examination. Examples of the body region to be examined are the abdomen, thorax or neck. Basically, it is also conceivable that the body region to be examined relates also to organs such as the patient's liver, heart, gall bladder or thyroid gland. Typically, the sensor may simply sense a surface of the patient's body and for example determine the corresponding body region via image recognition. In order to localize the organs of the patient, an alternative imaging system, for example an X-ray-based fluoroscopy system or preferably an ultrasound system, may be required in certain cases.

Depending on specification, the ultrasound examination may be performed using different ultrasound probes. Ultrasound images may be determined from the ultrasound measurement data generated in the process, which data substantially corresponds to the electrical receive signals. The determined ultrasound images may be evaluated and visualized in different ways, a process referred to as the mode (method). In addition to the A mode (amplitude curve of the ultrasound measured data), a two-dimensional sectional image (slice) of the body region to be examined is often generated in real-time. The form of the determined ultrasound image may be dependent on the ultrasound probe. A temporal resolution of the ultrasound examination is typically a function of further measurement parameters of the ultrasound examination, such as the penetration depth of the pressure pulses transmitted by the ultrasound probe and the ultrasound probe used. Alternatively or in addition, the B mode, M mode and/or a Doppler method may also be applied in an ultrasound examination, including in combination. All of these methods are well-known to the person skilled in the art.

One specification for the ultrasound examination may comprise for example an aim of the ultrasound examination. The aim of the ultrasound examination may be to detect a space-occupying lesion in an organ during the follow-up period. In the follow-up, a medical examination is typically performed a number of times, in particular over a relatively long period of time. Because the application is typically low-risk, non-invasive, painless and involves no exposure to ionizing radiation, the multiple repetition of the medical examination poses no health risk to the patient. For example, the space-occupying lesion, in particular a tumor or a node, may be detected in an ultrasound examination before, during and after the treatment with medication. The specification for the ultrasound examination may furthermore be the recording of the cardiac blood flow or the size of the heart.

In an embodiment, the medical issue comprises patient-specific data of a patient. The patient-specific data includes at least one parameter from the following list:
a body height of the patient,
a weight of the patient,
medical findings pertaining to the patient, and
medical image datasets of the patient.

The patient-specific data may in this way comprise at least one anatomical characteristic indicator of the patient, such as the patient's body height and/or the patient's weight, for example. The motion sequence of the robot arm may be tailored particularly suitably to match the at least one anatomical characteristic indicator of the patient. For example, the motion sequence may be shorter in terms of space covered in the case of a slimmer patient. As a further example, the motion sequence may be longer in terms of space covered if the patient is of heavier stature.

Furthermore, the patient-specific data may include the patient's age. The age of the patient may for example influence the specification of the medical issue. The specification may therefore be a criterion which in particular specifies or characterizes the manner in which the ultrasound examination is actually performed. For example, the specification may request an ultrasound examination of preferably short duration. The ultrasound examination of preferably short duration is in particular advantageous when the patient to be examined is unable to lie still for a sufficiently long time because the patient is of a comparatively advanced age. In other words, the duration of the motion sequence is in particular shorter, the older the patient. In such a case it may namely be possible to perform the ultrasound examination more quickly.

Typically, much of the information about the patient, generated for example during ultrasound examinations, is evaluated with reference to the patient and stored. A user, for example a physician treating the patient, describes a medical condition of the patient in a clinical finding. The clinical finding may typically contain an indication as to a disorder (type, severity, etc.) as well as descriptive parameters (size of the space-occupying lesion, blood pressure, etc.). If, at a subsequent medical examination, the clinical finding is present with a further medical issue, the physician may learn about a medical history of the patient in particular by way of the clinical findings. The medical history may include a plurality of clinical findings which have been produced on different occasions by different persons, in particular physicians. The patient-specific data may therefore include for example the follow-up of the tumor disease or a medication plan. For example, the motion dataset may be determined according to the follow-up in such a way that the follow-up can be continued by way of the ultrasound examination.

Medical image datasets of the patient that were acquired prior to the ultrasound examination may be relevant to the medical issue. For example, medical image datasets may have been acquired by different medical imaging devices. Furthermore, medical image datasets may also include typical camera footage of the surface of the patient's body. Taking the medical image datasets into consideration, a motion dataset may preferably be determined in such a way that the ultrasound examination may be performed with high-quality results.

For reasons of clarity, the statements made in relation to the at least one medical training issue are not presented separately because these substantially correspond to the statements made in relation to the medical issue. This means in essence that the medical training issue and the medical issue may be consistent with one another in terms of their data format except for the time of the respective recording.

The robot arm typically has suitable attachment device(s) to ensure that the ultrasound probe can be mounted on the robot arm by way of the attachment device(s).

The robot arm is preferably embodied in such a way that it is able to perform the typical movements of a human user. For example, the robot arm may have at least one revolute joint and at least one carrier element for this purpose. It is also conceivable that the robot arm has at least one telescope unit which can be retracted and extended. The ultrasound probe may for example be mounted on the at least one carrier element. Given suitable configuration of the robot arm, the robot arm has at least one degree of freedom. Typically, the robot arm comprises a sufficient number of degrees of freedom to ensure that the robot arm is able to perform a task that it has been set. Performing the task that the robot arm has been set usually comprises moving the robot arm in accordance with a motion dataset.

The robot arm normally has a robot arm coordinate system containing a 3D range of motion of the robot arm in which the robot arm may be moved. The motion dataset determined by the trained neural network is preferably adapted to match the 3D range of motion of the robot arm. The 3D range of motion of the robot arm is predefined in particular by the embodiment of the robot arm with regard to envisioned degrees of freedom of the robot arm. The 3D range of motion may have been measured by way of a calibration run, for example. The 3D range of motion of the robot arm may differ depending on the type and configuration of the robot arm.

The neural network can provide an output at the output layer as a function of the input at the input layer. Typically, the recorded medical issue is input at the input layer of the provided trained artificial neural network. The medical issue may be input as input information into the trained artificial neural network. As output, in particular as output of the artificial neurons of the output layer, the artificial neural network may determine the motion dataset. In other words, the motion dataset, as output of the artificial neurons of the output layer, is assigned to the medical issue. Providing the output at the output layer following input at the input layer may be equivalent to an assigning of the motion dataset as a function of the medical issue if the artificial neural network is applied to the medical issue in such a way that the medical issue is input as input information at the input layer of the artificial neural network and a motion dataset is determined on the basis thereof.

This approach is based in particular on the consideration that the motion dataset may be read out by way of the medical issue. As it is possible for a human user, in particular a physician, to ascertain, solely on the basis of the medical issue, with which motion dataset the ultrasound examination may be performed, in the same way the correspondingly trained artificial neural network can extract this information likewise solely on the basis of the medical issue.

The motion dataset determined by the application of the artificial neural network is transferred to the controller of the robot arm. The motion dataset may be present in a suitable data format, which is transferred from the output layer of the neural network directly or indirectly to the controller of the robot arm. Typically, the controller of the robot arm can process the motion dataset in a suitable manner as soon as the motion dataset has been transferred.

The motion dataset comprises the motion sequence of the robot arm. In addition, the motion dataset may contain a configuration in respect of the extent to which the motion sequence includes a spatial tolerance in the event of a deviation from the predefined motion sequence.

In a further embodiment, the motion sequence of the robot arm comprises the function of the orientation of the robot arm over time and the function of the position of the robot arm over time. The motion sequence may therefore in particular describe the motion of the robot arm. The position of the robot arm, in particular a midpoint or an endpoint of the robot arm, can typically be specified by way of coordinates in a three-dimensional coordinate system having an arbitrary point of origin. The orientation of the robot arm may be specified in particular according to a solid angle between for example a robot axis extending in the longitudinal direction of the robot arm and a system plane which is defined by the coordinate system.

A combination of position and orientation is often referred to in the technical context as the pose or location in 3D space. The function of the location in 3D space over time therefore corresponds in particular to the function of the orientation over time together with the function of the position over time. The motion sequence may therefore comprise at least one location in 3D space over time. For example, a robot controller may receive or send motion sequences via an interface. The motion sequences of the robot arm can be translated directly into the function of the orientation of the robot arm over time and the function of the position of the robot arm over time.

The controller is able to move the robot arm in accordance with the motion sequence of the motion dataset, for example in that the controller sends control signals corresponding to the motion sequence to the robot arm. In particular, the robot arm can move along the locations in 3D space corresponding to the motion sequence. The robot arm therefore preferably travels to the locations in 3D space, in particular the positions and orientations specified by the temporal function. Accordingly, the controller preferably controls the movement of the robot arm in accordance with the motion sequence of the motion dataset. Preferably, the robot arm is moved on the surface of the patient's body. If the medical issue concerns a specific body region, the robot arm is moved according to the specific body region.

For reasons of clarity, the statements made in relation to the at least one training motion dataset are not presented separately because these substantially correspond to the statements made in relation to the motion dataset.

Analogously, a training motion sequence substantially corresponds to the motion sequence.

In a further embodiment, the robot arm has attachment device(s) for a projector. The projector is preferably connected to the robot arm in a releasable manner by way of the attachment device(s). Basically, it is also conceivable that the robot arm actuates an external projector which is not mounted on the robot arm, via a cable connection, for example. For example, the projector may project the motion sequence onto the surface of the patient's body by way of laser light.

Basically, it is also conceivable that the projector supports the user during the recording of the medical issue. For example, the projector can mark or illuminate the body region to be examined of the patient with light.

According to a further embodiment, the robot arm has a sensor. Alternatively, it is also conceivable that the robot arm has attachment device(s) for the sensor, the sensor being able to be releasably mounted on the robot arm by way of the attachment device(s). The sensor comprises at least one of the following variants: an electrooptical sensor, a camera, a device for recording an electrocardiogram, a distance sensor, a pose sensor, and a pressure sensor. The sensor is able to detect the location of the robot arm in 3D space. Typically, the sensor can detect whether the motion sequence of the robot arm is compromised by an obstacle. The sensor normally offers a feedback device(s) during the movement of the robot arm.

The pose sensor can capture the motion sequence of the robot arm, in particular the function of the orientation of the robot arm over time and the function of the position of the robot arm over time. Alternatively or in addition, the sensor may have an acceleration sensor. Basically, it is conceivable that the robot arm has a plurality of sensors. For example, the robot arm may have a first pose sensor for a robotic joint, which may correspond to the at least one revolute joint of the robot arm, and a second pose sensor as well as an acceleration sensor in the ultrasound probe.

For example, the pressure sensor can determine whether the robot arm is moving freely or for example is being pressed too firmly against the patient. For example, the robot arm may have a suitable device, for example a collision sensor, or an algorithm that can detect a collision of the robot arm with the patient via the sensor. For example, a respiratory motion of the patient can be detected. The respiratory motion of the patient is captured for example by way of a respiratory belt for detecting the respiratory motion or by way of the camera.

The controller can capture the motion sequence via the sensor. Alternatively or in addition, the controller can calculate and acquire the motion sequence by way of suitable algorithms. In particular, the controller of the robot arm possesses suitable algorithms which can capture, in particular calculate, the location of the robot arm in 3D space.

Normally, the controller validates the determined motion dataset in terms of performability. The controller may access further information of the sensor for this purpose. The motion dataset can be adjusted by the controller to match the 3D range of motion of the robot arm. If no adjustment is possible, the controller may for example interrupt the ultrasound examination and/or return an error message. The 3D range of motion of the robot arm typically comprises the 3D range of motion of the ultrasound probe which is attached to the robot arm. The ultrasound probe may be moved within the ultrasound probe's 3D range of motion.

The validation of the motion dataset by the controller of the robot arm may comprise the controller correcting the determined motion dataset by way of the data provided by the sensor, from which images are reconstructed for example, in such a way that the motion dataset is tailored to the surface of the patient's body. This may serve in particular toward a better performance of the ultrasound examination if for example the patient has become older or more ill or slimmer for example in the time since the training of the artificial neural network. For the validation of the motion dataset, it may be relevant that ultrasound images that are suitable for the medical issue may be generated by the ultrasound examination.

In particular, the controller of the robot arm transmits suitable control signals so that the robot arm is moved. When the robot arm is moved, it may typically be moved via the robot arm's motors and/or actuators and/or sensors.

In a further embodiment variant, the robot arm is moved automatically in accordance with the motion sequence of the motion dataset. It is therefore conceivable that only the robot arm is situated in an examination room with the patient. A person supervising the procedure may be present in the examination room. It would also be conceivable that the supervising person enables the automatic movement of the robot arm. For example, the robot arm is moved in accordance with the motion sequence only while the supervising person enables the movement of the robot arm, in particular by actuating a safety device. As soon as the supervising person interrupts the enabling of the movement, in particular the movement in accordance with the motion sequence is likewise interrupted. After an interruption to the enabling by the supervising person, the movement of the robot arm in accordance with the motion sequence is normally resumed.

Alternatively or in addition, the safety device may be actuated by the supervising person outside of the examination room. Preferably, the supervising person may be situated at an arbitrary location, the supervising person having for example a suitable network connection available and a correspondingly configured display device which enable the ultrasound examination to be monitored from outside of the examination room. For example, it is also conceivable that the supervising person performs an intervention or a surgical procedure on the patient. In this case the robot arm may be maneuvered automatically, while for example the supervising person, in particular the physician, performs the intervention or the surgical procedure.

According to a further embodiment, the deviation of a movement of the robot arm from the motion sequence of the motion dataset during the movement of the robot arm is determined by way of the sensor. The deviation from the motion sequence may be detected via a suitable sensor, in particular in real-time. An actual location in 3D space, in particular an actual motion sequence, of the robot arm may deviate from the location in 3D space predefined by the motion sequence at an arbitrary point in time, for example because the patient is breathing.

The controller has in particular device(s) for initiating countermeasures if the movement of the robot arm deviates from the motion sequence of the motion dataset. For example, the controller can adjust the motion sequence of the robot arm and initiate countermeasures according to the determined deviation, for example according to the respiratory motion of the patient. Typically, the controller can calculate corrective control signals according to the device for recording the echocardiogram. Initiating countermeasures may mean that the controller calculates corrective control signals and sends the corrective control signals to the robot arm, the robot arm being moved according to the corrective control signals. The controller can normally calculate suitable corrective control signals irrespective of the reason why the deviation from the motion sequence has arisen, and send the signals to the robot arm.

According to a further embodiment, the robot arm is moved by the user in accordance with the motion sequence of the motion dataset. For example, the user may move the robot arm when the user is guiding the ultrasound probe by way of at least one of his/her hands during the ultrasound examination. The robot arm may provide a suitable guidance device which the user takes in at least one hand or is able to guide with at least one hand. The maneuvering of the robot arm may correspond to a guiding of the ultrasound probe by the user. The ultrasound probe may be guided in such a way that the user can guide the ultrasound probe with at least one hand or the user guides the suitable guidance device with at least one hand, the ultrasound probe being maneuvered via a direct operative connection between the suitable guidance device and the robot arm. For example, the user may guide the ultrasound probe either directly or by way of the suitable guidance device. The direct operative connection may comprise device(s) to ensure that the robot arm and/or the ultrasound probe attached to the robot arm are/is moved when the suitable guidance device is moved. The direct operative connection may include a lever, for example.

The moving of the robot arm in accordance with the motion sequence of the motion dataset by the user comprises supporting the user during the movement of the robot arm in accordance with the motion sequence of the motion dataset, for example when a dead weight of the robot arm is compensated for by the controller. Preferably, the user can conduct the ultrasound examination without any interference caused by the robot arm to which the ultrasound probe is attached. The interference caused by the robot arm may be due to a missing degree of freedom of the robot arm. Alternatively or in addition, the interference may consist of a resistance during the moving of the robot arm, which resistance typically may result due to the friction in a revolute joint for example or when a telescope unit is retracted and extended. Preferably, the user guiding the ultrasound probe is free when moving the robot arm, in particular when guiding the ultrasound probe. In other words, the user is supported in such a way that without exerting any additional force the user is able to move the robot arm in accordance with the motion sequence of the motion dataset as though the ultrasound probe were not attached to the robot arm.

If a motion dataset has been determined by applying the artificial neural network to the medical issue and if the movement of the robot arm deviates from the motion sequence of the motion dataset, the user may for example be supported in such a way that the controller of the robot arm draws the user's attention thereto. For example, the robot arm may have a vibration device which alerts the user by way of a vibration if the movement of the robot arm deviates from the motion sequence of the motion dataset. Alternatively or in addition, it would also be conceivable that the robot arm indicates the motion sequence of the determined motion dataset to the user by way of an optical device, in particular a lamp or a laser, or by way of the projector. The lamp could for example light up in the event of a deviation from the motion sequence of the determined motion dataset. Alternatively or in addition, the laser can project the motion sequence of the determined motion dataset in particular onto the surface of the patient's body.

In a further embodiment, it is conceivable that the robot arm can be moved in accordance with the motion sequence of the motion dataset both automatically and by the user. In this case the robot arm may have both the suitable guidance device and for example the safety device, which the robot arm usually has when the robot arm can be moved automatically. For example, depending on the ultrasound examination, either the user can move the robot arm in accordance with the motion sequence of the motion dataset or the robot arm is moved automatically in accordance with the motion sequence of the motion dataset.

In addition, the trained artificial neural network is provided in accordance with the inventive method for providing a trained artificial neural network for the purpose of determining a motion dataset containing a motion sequence of a robot arm for an ultrasound examination, an ultrasound probe being attached to the robot arm. In this way a particularly advantageously trained artificial neural network may be provided for the task of determining a motion dataset by applying the trained artificial neural network to the medical issue.

At least one embodiment of the method for providing a trained artificial neural network for the purpose of determining a motion dataset containing a motion sequence of a robot arm for an ultrasound examination, an ultrasound probe being attached to the robot arm, comprises:
    providing at least one training motion dataset, wherein at least one medical training issue is assigned to the at least one training motion dataset,
    training an artificial neural network using the at least one training motion dataset and the at least one medical training issue,
wherein the application of the trained artificial neural network to the at least one medical training issue enables the at least one training motion dataset to be determined, and
    providing the trained artificial neural network for the purpose of determining the motion dataset.

The at least one training motion dataset and the at least one medical training issue, at least one medical training issue being assigned to the at least one training motion dataset, are therefore crucial for the training of the artificial neural network.

In particular, the at least one medical training issue has already been assigned to the at least one training motion dataset. Otherwise, the at least one medical training issue may be assigned to the at least one training motion dataset manually or automatically. The assignment of the at least one medical training issue to the at least one training motion dataset may in this case be carried out for example by a manufacturer of the sensor by which the motion datasets have been acquired, and/or by a user who generated the motion datasets based on examinations, or by a member of staff in a hospital.

Typically, the at least one medical training issue, in particular patient-specific data, is available for the at least one training motion dataset. For example, an image format (e.g. DICOM) may include patient-specific data, in particular medical issues, in addition to the image information. In particular, only the at least one training motion dataset is used for the training of the artificial neural network to which the at least one medical training issue is assigned, the at least one medical training issue containing sufficient information for the training.

The acquisition of the at least one training motion dataset and the providing of the at least one training motion dataset may preferably be effected by way of the sensor, for example the pose sensor and/or the acceleration sensor. The acquisition of the at least one training motion dataset typically precedes the providing of the at least one training motion dataset. For example, the sensor initially acquires the at least one training motion dataset, in which the motion sequence is captured, and in a next step in particular a controller of the sensor provides the training motion dataset via a suitable interface.

According to one embodiment variant, the providing of the at least one training motion dataset by the user comprises manually performing the at least one training ultrasound examination by way of the robot arm based on the at least one medical issue and capturing the training motion sequence of the at least one training motion dataset during the at least one manually performed training ultrasound examination.

The manual performance of the at least one training ultrasound examination by way of the robot arm is typically accomplished by the user. For example, the user can move the ultrasound probe via the guidance device of the robot arm. Typically, the at least one training ultrasound examination is based on the at least one medical training issue.

As the robot arm is moved, the training motion sequence, in particular the locations in 3D space traversed over time, can be stored. When the at least one training ultrasound examination is performed manually, the training motion sequence can be captured by way of the robot arm, in particular the controller of the robot arm, based on the at least one medical training issue. The training motion sequence captured in this case based on the at least one medical training issue can necessarily be translated into the at least one training motion dataset. The at least one training motion dataset then preferably contains the training motion sequence in accordance with which the robot arm was moved by the user when manually performing the at least one training ultrasound examination based on the at least one medical training issue. The at least one medical training issue can therefore be assigned to the at least one training motion dataset during the manual performance of the at least one training ultrasound examination.

According to a further embodiment variant, the providing of the at least one training motion dataset by the user may alternatively or additionally comprise the exclusively manual performance of at least one training ultrasound examination by way of a free ultrasound probe which is not attached to the robot arm based on the at least one medical training issue, wherein the user moves the free ultrasound probe, the movements of the free ultrasound probe are captured via a sensor during the at least one training ultrasound examination, and the captured movements are translated into at least one training motion dataset which can be performed by way of the robot arm.

The at least one training ultrasound examination may for example be performed without the ultrasound probe which is attached to the robot arm. For example, the free ultrasound probe may also correspond to the ultrasound probe attached to the robot arm if the otherwise free ultrasound probe is attached to the robot arm. Basically, the free ultrasound probe may also be a second ultrasound probe in addition to the ultrasound probe attached to the robot arm. Furthermore, it is also possible that only the free ultrasound probe is available with an associated ultrasound system in a training room and the robot arm is located in the examination room.

The movements of the free ultrasound probe during the at least one training ultrasound examination are captured via a sensor, for example a camera. The capturing of the movements may correspond to the storing of motion data. The motion data typically corresponds to the captured movements, in particular to the location in 3D space of the free ultrasound probe over time during the at least one training ultrasound examination. According to the location in 3D space of the free ultrasound probe over time, it is possible to determine the motion sequence which is translated into the at least one training motion dataset which can be performed by way of the robot arm. The translation of the acquired motion data, in particular of the captured movements, typically corresponds to a conversion of the motion data, in particular of the movements, into the at least one training motion dataset which can be performed by way of the robot arm. Preferably, the 3D range of motion of the robot arm is taken into account in the conversion.

The training of the artificial neural network is advantageously accomplished by backpropagation. This means in particular that the at least one training issue is fed in as input data into the artificial neural network that is to be trained. During the training, an output of the artificial neural network to be trained is then compared with the at least one training dataset which is assigned to the at least one training issue. The output of the artificial neural network to be trained preferably comprises the at least one training motion dataset. The training of the artificial neural network then comprises in particular making a change to the network parameters of the artificial neural network to be trained in such a way that the output of the artificial neural network to be trained lies closer to the at least one training dataset to which the at least one training issue is assigned. The artificial neural network is therefore advantageously trained in such a way that the at least one training motion dataset assigned to the at least one training issue is determined through the application of the artificial neural network to the at least one training issue.

While the backpropagation normally represents the most important training algorithm for training the artificial neural network, other algorithms known to the person skilled in the art may also be used for training the artificial neural network. Examples of other possible algorithms are evolutionary algorithms, "simulated annealing", "expectation maximization" algorithms (EM algorithms), parameter-free algorithms (non-parametric methods), particle swarm optimization (PSO), etc.

The training of the artificial neural network may take place entirely at the robot arm manufacturer's facility and/or at the organization carrying out the training. Alternatively, it is also conceivable for a preliminary training phase to take place at the robot arm manufacturer's facility and/or at the organization initially carrying out the training, and a post-training phase to be scheduled on one or more occasions in a hospital in order to make the process of determining the motion dataset even more robust specifically for the requirements of the hospital. It is equally conceivable to repurpose an already trained artificial neural network for a different classification task by importing new weight matrices.

It is also conceivable for the training of the artificial neural network to be carried out in a number of iterations. In this way, a providing of the at least one training motion dataset, wherein at least one medical training issue is assigned to the at least one training motion dataset, and the training of the artificial neural network can be carried out in alternation in multiple steps. Thus, for example, a selectivity in the determining of the motion dataset can be improved by way of the trained artificial neural network.

The artificial neural network trained in this way may subsequently be used in a method according to at least one embodiment of the invention for determining a motion dataset by applying the trained artificial neural network to a medical issue or be provided for that purpose. In this way the described training of the artificial neural network enables motion datasets which are not yet known in advance to be determined subsequently in a particularly advantageous manner as a function of medical issues.

Typically, in at least one embodiment, the method for providing a trained artificial neural network may provide that a validity check is performed on the trained artificial neural network before the trained artificial neural network is provided. The validity check may be performed only with a sample. By way of the check it can be ensured that the trained artificial neural network is suitable for determining a motion dataset.

The ultrasound system of at least one embodiment comprises a planning unit, a first computing unit and a measurement unit which has a robot arm for an ultrasound examination, an ultrasound probe being attached to the robot arm.

The planning unit may comprise the monitor with the graphical user interface and the input device. Typically, the user is able to interact with the planning unit, in particular via the input device. For example, the user may also view ultrasound measurement data or ultrasound images of the ultrasound examination on the monitor. The planning unit can display ultrasound measurement data in particular on the monitor.

The first computing unit is preferably configured in such a way that it can determine the motion dataset by applying the artificial neural network to the medical issue. The computing unit may have interfaces to the planning unit, to the controller or to the measurement unit, wherein the medical issue and/or the motion dataset can in particular be received and sent via the interfaces. The first computing unit is preferably embodied in such a way that the trained neural network, which is provided for example as a computer program product and can be loaded into a memory of the first programmable computing unit, is executable on the first computing unit.

The measurement unit comprises the robot arm for the ultrasound examination. The ultrasound probe is attached to the robot arm. The measurement unit normally comprises the robot arm and the controller of the robot arm. The measurement unit may comprise the sensor, the camera and/or the projector. The ultrasound system is preferably embodied for moving the robot arm for the purpose of the ultrasound examination.

Most of the components of the ultrasound system according to at least one embodiment of the invention may be embodied in the form of software components. In principle, however, some of these components may also be realized in the form of software-assisted hardware components, for example FPGAs or the like, in particular when there is a requirement for particularly fast calculations. Similarly, the required interfaces may be embodied as software interfaces, for example when it is simply a matter of importing data from other software components. However, they may also be embodied as hardware-based interfaces which are controlled by suitable software. It goes without saying that it is also conceivable for a plurality of the cited components to be realized in combination in the form of a single software component or software-assisted hardware component.

The second computing unit according to at least one embodiment of the invention is embodied for providing a trained artificial neural network for the purpose of determining a motion dataset containing a motion sequence of a robot arm for an ultrasound examination, an ultrasound probe being attached to the robot arm. Preferably, the second computing unit is able to perform a method according to the invention for providing a trained artificial neural network. The second computing unit comprises a computing module. The computing module may be used for example for the training of the artificial neural network.

The computer program product according to at least one embodiment of the invention can be loaded directly into a memory of a programmable computing unit and has program code segments for performing a method according to at least one embodiment of the invention when the computer program product is executed in the computing unit. The first computing unit and the second computing unit are equivalent to such a programmable computing unit and each have a memory.

The computer program product may be a computer program or comprise a computer program. This enables at least one embodiment of the method according to the invention to be performed quickly and in an identically reproducible and robust manner. The computer program product is configured in such a way that it can perform at least one embodiment of the inventive method steps by way of the computing unit. The computing unit must in each case provide the prerequisites for this, such as a corresponding random access memory, for example, a corresponding graphics card or a corresponding logic unit, so that the respective method steps can be performed efficiently.

The computer program product is stored, for example in at least one embodiment, on a non-transitory computer-readable medium or held resident on a network or server, from where it can be loaded into the processor of the computing unit, which processor may be embodied for example as part of the ultrasound system. Control information of the computer program product may also be stored on an electronically readable data medium. The control information of the electronically readable data medium may be embodied in such a way that it performs a method according to at least one embodiment of the invention when the data medium is used in a computing unit. Thus, the computer program product may also represent the electronically readable data medium.

Examples of non-transitory electronically readable data media include, but are not limited to, a DVD, a magnetic tape, a hard disk or a USB stick on which electronically readable control information, in particular software (cf. above), is stored. When the control information (software) is read from the data medium and stored in a first computing unit and/or planning unit and/or measurement unit of the ultrasound system and/or second computing unit, all of the inventive embodiment variants of the methods described hereinabove may be performed. Accordingly, the invention may also relate to the the computer-readable medium and/or the electronically readable data medium.

Further features, advantages or alternative embodiment variants of the method according to at least one embodiment of the invention for determining a motion dataset by applying a trained neural network to a medical issue and/or of the associated ultrasound system and/or of the method according to at least one embodiment of the invention for providing a trained artificial neural network and/or of the associated second computing unit and/or of the computer program product may equally be applied also to the respective other claimed subject matters, and vice versa.

FIG. 1 shows an ultrasound system 11, the ultrasound system 11 having a robot arm 14 and a sensor, in particular a camera 16. An ultrasound probe 15 is attached to the robot arm 14. The robot arm 14 is preferably embodied in such a way that an ultrasound examination of a patient 12 may be performed by way of the robot arm 14. Preferably, the patient 12 is positioned on a patient support device 13, in particular on a patient couch. Typically, the patient 12 lies supine on the patient couch. Alternatively, the patient 12 may also adopt a sitting position during the ultrasound examination.

The ultrasound system 11 comprises a planning unit 17, a first computing unit 18 and a measurement unit 19. The measurement unit 19 has in particular the robot arm 14 for an ultrasound examination, the ultrasound probe 15 being attached to the robot arm 14. The robot arm 14 has in particular a controller 20 of the robot arm 14 and the camera 16.

A free ultrasound probe 15.*f* is not connected to the robot arm 14. When the free ultrasound probe 15.*f* is connected to the robot arm 14, the formerly free ultrasound probe 15.*f* then corresponds to the ultrasound probe 15. The free ultrasound probe 15.*f* is part of a separate ultrasound system.

The free ultrasound probe 15.*f* may for example be used by the user for providing training motion datasets. According to a preferred embodiment, the user may conduct at least one training ultrasound examination exclusively manually by way of the free ultrasound probe 15.*f*, which is not attached to the robot arm 14, based on the at least one medical training issue, the user moving the free ultrasound probe 15.*f*. In that case the movements of the free ultrasound probe 15.*f* during the at least one training ultrasound examination are captured via a sensor, in particular the camera 16, and the captured movements are translated into at least one training motion dataset which can be performed by way of the robot arm 14.

For example, it is also conceivable that the user performs a first ultrasound examination using the free ultrasound probe 15.*f* and the robot arm 14 performs a second ultrasound examination according to the first ultrasound examination. In other words, the robot arm 14 can initially record the first ultrasound examination and thereupon preferably repeat the same by performing the second ultrasound examination.

The robot arm 14 additionally has a first carrier element 14.1 having a length L1 and a second carrier element 14.2 having a length L2. The first carrier element 14.1 is arranged on a suspension device 14.*a*. The second carrier element 14.2. is connected to the first carrier element 14.1. The suspension device 14.*a* is embodied in a disk shape and an x-axis and a y-axis of a coordinate system lie in the suspension device 14.*a*. The z-axis stands perpendicularly on a plane which is formed by the x-axis and the y-axis of the coordinate system. A first angle W1 describes an angle between the x-axis and the y-axis. A second angle W2 describes an angle between a longitudinal axis extending in the longitudinal direction of the first carrier element 14.1 and the z-axis. A third angle W3 describes an angle between the longitudinal axis extending in the longitudinal direction of the first carrier element 14.1 and a longitudinal axis extending in the longitudinal direction of the second carrier element 14.2. The reference point 14.*p* corresponds to an end of the second carrier element 14.2 which is not connected to the first carrier element 14.1.

The controller 20 captures the motion sequence by way of suitable algorithms, for example. The position in (x,y,z) coordinates of the reference point 14.*p* can be calculated for example using the following equation:

$$x_{14,p} = \cos(W1) \cdot (L2 \sin(W2+W3) + L1 \sin(W2))$$

$$y_{14,p} = \sin(W1) \cdot (L2 \sin(W2+W3) + L1 \sin(W2))$$

$$z_{14,p} = L2 \cos(W2+W3) + L1 \cos(W2)$$

In addition, the orientation of the robot arm 14 can preferably be determined by way of suitable algorithms. The orientation typically corresponds to a solid angle of the robot arm 14 and can be calculated from the angles W1, W2 and W3.

$$c = \frac{x^2 + y^2 + z^2 - (L_1)^2 - (L_2)^2}{2L_1 L_2}$$

$$W1 = \tan^{-1}\left(\frac{y}{x}\right)$$

$$W2 = 90° - \tan^{-1}\left(\frac{z}{\sqrt{x_2 + y_2}}\right) + \tan^{-1}\left(\frac{L2\sqrt{1-c^2}}{L_1 + L_2 c}\right)$$

$$W3 = \tan^{-1}\left(\frac{\sqrt{1-c^2}}{c}\right)$$

The robot arm 14 may have further degrees of freedom (not shown) by way, for example, of at least one revolute joint or at least one telescope unit.

The controller 20 can process the determined motion dataset in such a way that the robot arm is moved in accordance with the motion sequence of the robot arm.

The illustrated ultrasound system 11 may of course comprise further components that are ordinarily present in ultrasound systems 11. Equally, the individual components, in particular the robot arm 14, the ultrasound probe 15, the camera 16, the planning unit 17, the first computing unit 18, the measurement unit 19 and the controller 20, may be disposed in a different relationship to one another and/or be integrated into a higher-ranking unit. The general principle of operation of an ultrasound system 11 is furthermore known to the person skilled in the art, so a detailed description of the further components is dispensed with.

Figure 2:
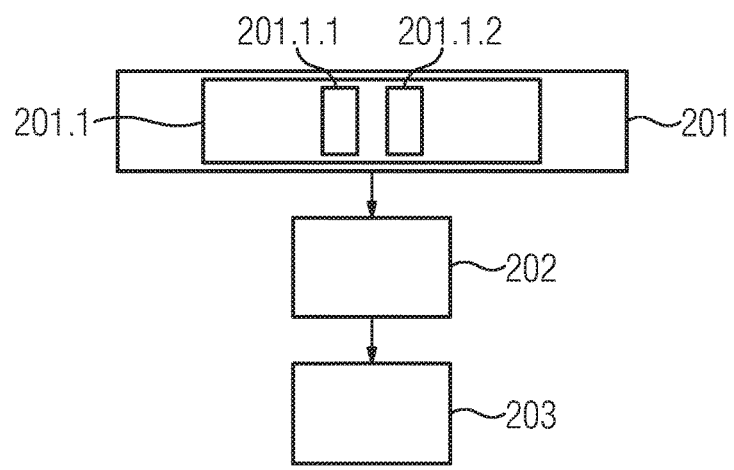
FIG. 2 shows a flowchart of a method according to an embodiment of the invention for providing a trained artificial neural network.
Figure 3:
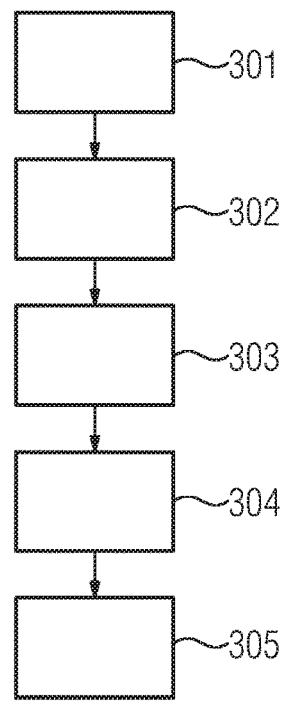
FIG. 3 shows a flowchart of a method according to an embodiment of the invention for moving a robot arm.

The ultrasound system is preferably embodied also to separately perform the method steps depicted in both FIG. 2 and FIG. 3.

FIG. 2 shows a flowchart of a method according to an embodiment of the invention for providing a trained artificial neural network for determining a motion dataset containing a motion sequence of a robot arm 14 for an ultrasound examination, an ultrasound probe 15 being attached to the robot arm 14. The method comprises the method steps 201-203 and the respective subordinate method steps.

Method step 201 designates the providing of at least one training motion dataset, wherein at least one medical training issue is assigned to the at least one training motion dataset.

Method step 202 designates the training of an artificial neural network using the at least one training motion dataset and the at least one medical training issue, wherein the application of the trained artificial neural network to the at least one medical training issue enables the at least one training motion dataset to be determined.

Method step 203 designates the providing of the trained artificial neural network for the purpose of determining the motion dataset.

Subordinate method step 201.1 designates the providing of the at least one training motion dataset by a user. The providing 201.1 of the at least one training motion dataset by the user comprises the following subordinate method steps:

manually performing 201.1.1 at least one training ultrasound examination by way of the robot arm (14) based on the at least one medical training issue, capturing 201.1.2 a training motion sequence of the at least one training motion dataset during the at least one manually performed training ultrasound examination.

A second computing unit for providing a trained artificial neural network comprises a computing module, the second computing unit being embodied for performing a method according to method steps 201-203 as well as subordinate method steps 201.1, 201.1.1 and 201.1.2.

The method steps of the method according to an embodiment of the invention shown in FIG. 2 are performed by the second computing unit. To that end, the second computing unit comprises requisite software and/or computer programs and/or a computer program product, which are stored in a memory unit of the second computing unit. The software and/or computer programs and/or the computer program product comprise program segments which are configured to perform the method according to the invention when the computer program and/or the software and/or the computer program product are/is executed in the second computing unit via a processor unit of the second computing unit.

FIG. 3 shows a flowchart of a method according to an embodiment of the invention for moving a robot arm 14 for an ultrasound examination, an ultrasound probe 15 being attached to the robot arm 14. The method comprises the method steps 301-305.

Method step 301 designates the providing of a trained artificial neural network.

Method step 302 designates the recording of a medical issue. The recording of the medical issue preferably comprises a sensor and/or a user providing at least one parameter of the medical issue via a graphical user interface. The medical issue includes at least one parameter from the following list:
- a body region to be examined of a patient 12,
- a mode of the ultrasound examination,
- a frequency of the ultrasound examination, and
- a specification for the ultrasound examination.

According to a further embodiment variant, the medical issue comprises patient-specific data of a patient 12 and the patient-specific data includes at least one parameter from the following list:
- a body height of the patient 12,
- a weight of the patient 12,
- a clinical finding on possible disorders of the patient 12, and
- a medical image dataset of the patient 12.

In a further embodiment, the motion sequence of the motion dataset includes a function of the orientation of the robot arm 14 over time and a function of the position of the robot arm 14 over time.

Preferably, the robot arm 14 has a sensor and the sensor comprises at least one of the following variants:
- an electrooptical sensor,
- a camera 16,
- a distance sensor,
- a pose sensor, and
- a pressure sensor.

Method step 303 designates the determining of a motion dataset containing a motion sequence of the robot arm 14 through application of the trained artificial neural network to the medical issue.

Method step 304 designates the transferring of the motion dataset to a controller 20 of the robot arm 14.

Method step 305 designates the moving of the robot arm 14 in accordance with the motion sequence of the motion dataset. According to a preferred embodiment, the robot arm 14 is moved automatically and/or by a user in accordance with the motion sequence of the motion dataset and the moving of the robot arm 14 in accordance with the motion sequence of the motion dataset comprises the determining of a deviation of a movement of the robot arm from the motion sequence of the motion dataset during the movement of the robot arm 14 via the sensor and the initiation of countermeasures by the controller 20 according to the determined deviation.

The moving of the robot arm 14 by the user in accordance with the motion sequence of the motion dataset preferably includes supporting the user during the movement of the robot arm 14 in accordance with the motion sequence of the motion dataset.

The method steps of the method according to an embodiment of the invention shown in FIG. 3 are performed by the first computing unit 18 of the ultrasound system 11. For this purpose, the first computing unit 18 comprises requisite software and/or computer programs and/or a computer program product which are/is stored in a memory unit of the first computing unit 18.

The software and/or computer programs and/or the computer program product comprise program segments which are configured to perform the method according to an embodiment of the invention when the computer program and/or the software and/or the computer program product are/is executed in the first computing unit via a processor unit of the first computing unit.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for moving a robot arm for a non-invasive ultrasound examination, an ultrasound probe being attached to the robot arm, the method comprising:
   providing a trained artificial neural network;
   recording a medical issue;
   determining a motion dataset containing a motion sequence of the robot arm by applying the trained artificial neural network to the medical issue;
   transferring the motion dataset to a controller of the robot arm; and moving the robot arm in accordance with the motion sequence of the motion dataset, wherein the motion sequence is projected onto a body surface of a patient via a projector.

2. The method of claim 1, wherein the recording of the medical issue includes receiving at least one parameter of the medical issue via a graphical user interface.

3. The method of claim 1, wherein the medical issue includes at least one parameter including at least one of:
- a body region to be examined of a patient,
- a mode of the ultrasound examination,
- a frequency of the ultrasound examination, and
- a specification for the ultrasound examination.

4. The method of claim 1, wherein the medical issue includes patient-specific data of a patient and wherein the patient-specific data includes at least one parameter including at least one of:
- a body height of the patient,
- a weight of the patient,
- a clinical finding on possible disorders of the patient, and
- a medical image dataset of the patient.

5. The method of claim 1, wherein the motion sequence of the motion dataset includes:
- a function of an orientation of the robot arm over time, and
- a function of a position of the robot arm over time.

6. The method of claim 1, wherein the moving of the robot arm in accordance with the motion sequence of the motion dataset is performed by a user and the moving of the robot arm by the user in accordance with the motion sequence of the motion dataset comprises:
- supporting the user during the moving of the robot arm in accordance with the motion sequence of the motion dataset.

7. The method of claim 1, wherein the robot arm includes a sensor and wherein the sensor comprises at least one of:
- an electrooptical sensor,
- a camera,
- a distance sensor,
- a pose sensor, and
- a pressure sensor.

8. The method of claim 7, wherein the robot arm is at least one of movable automatically and movable non-automatically in accordance with the motion sequence of the motion dataset and wherein the moving of the robot arm in accordance with the motion sequence of the motion dataset comprises:
- determining a deviation of a movement of the robot arm from the motion sequence of the motion dataset during the moving of the robot arm via the sensor, and
- initiating countermeasures by the controller according to the deviation determined.

9. An ultrasound system, comprising:
- a planning unit;
- a first computing unit; and
- a measurement unit, including a robot arm for a non-invasive ultrasound examination, an ultrasound probe being attached to the robot arm, the ultrasound system being embodied to perform at least:
  - providing a trained artificial neural network,
  - recording a medical issue,
  - determining a motion dataset containing a motion sequence of the robot arm by applying the trained artificial neural network to the medical issue,
  - transferring the motion dataset to a controller of the robot arm, and
  - moving the robot arm in accordance with the motion sequence of the motion dataset, wherein the motion sequence is projected onto a body surface of a patient via a projector.

10. A non-transitory computer readable medium storing program code segments for performing the method of claim 1 when executed on a computing unit.

11. The method of claim 2, wherein the at least one parameter of the medical issue is received from at least one sensor via a graphical user interface.

12. The method of claim 2, wherein the medical issue includes at least one parameter including at least one of:
- a body region to be examined of a patient,
- a mode of the ultrasound examination,
- a frequency of the ultrasound examination, and
- a specification for the ultrasound examination.

13. The method of claim 11, wherein the medical issue includes at least one parameter including at least one of:
- a body region to be examined of a patient,
- a mode of the ultrasound examination,
- a frequency of the ultrasound examination, and
- a specification for the ultrasound examination.

* * * * *